United States Patent
Yu et al.

(10) Patent No.: US 11,316,318 B2
(45) Date of Patent: *Apr. 26, 2022

(54) DUAL WAVELENGTH SURGICAL LASER SYSTEM

(71) Applicant: Boston Scientific Scimed, Inc., Maple Grove, MN (US)

(72) Inventors: Honggang Yu, San Jose, CA (US); Rongwei Jason Xuan, Fremont, CA (US); Jian James Zhang, Santa Clara, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 133 days.

This patent is subject to a terminal disclaimer.

(21) Appl. No.: 16/564,925

(22) Filed: Sep. 9, 2019

(65) Prior Publication Data

US 2019/0393669 A1 Dec. 26, 2019

Related U.S. Application Data

(63) Continuation of application No. 14/964,890, filed on Dec. 10, 2015, now Pat. No. 10,454,237.

(Continued)

(51) Int. Cl.
*H01S 3/109* (2006.01)
*H01S 3/00* (2006.01)
(Continued)

(52) U.S. Cl.
CPC .............. *H01S 3/109* (2013.01); *H01S 3/005* (2013.01); *H01S 3/105* (2013.01);
(Continued)

(58) Field of Classification Search
CPC ........... A61B 2018/00589; A61B 2018/00625; A61B 2018/20359; A61B 2018/2065;
(Continued)

(56) References Cited

U.S. PATENT DOCUMENTS 3,769,963 A * 11/1973 Goldman ................ A61F 9/008
600/476
5,249,192 A * 9/1993 Kuizenga ............... A61B 18/20
372/107

(Continued)

FOREIGN PATENT DOCUMENTS

CN 101128160 A 2/2008
CN 201054458 Y 4/2008
(Continued)

OTHER PUBLICATIONS

Wikipedia, Laser Construction, https://en.wikipedia.org/wiki/Laser_construction, accessed Jun. 9, 2021 (Year: 2021).*

*Primary Examiner* — Jonathan T Kuo
(74) *Attorney, Agent, or Firm* — Bookoff McAndrews, PLLC

(57) ABSTRACT

A surgical laser system includes a pump module configured to produce pump energy within an operating wavelength, a gain medium configured to convert the pump energy into first laser energy, a non-linear crystal (NLC) configured to convert a portion of the first laser energy into second laser energy, which is a harmonic of the first laser energy, an output, and a first path diversion assembly having first and second operating modes. When the first path diversion assembly is in the first operating mode, the first laser energy is directed along the output path to the output, and the second laser energy is diverted from the output path and the output. When the first path diversion assembly is in the second operating mode, the second laser energy is directed along the output path to the output, and the first laser energy is diverted from the output path and the output.

13 Claims, 8 Drawing Sheets

Related U.S. Application Data

(60) Provisional application No. 62/092,380, filed on Dec. 16, 2014.

(51) Int. Cl.
   *H01S 3/105* (2006.01)
   *A61B 18/00* (2006.01)
   *A61B 18/20* (2006.01)
   *H01S 3/042* (2006.01)
   *H01S 3/04* (2006.01)
   *H01S 3/11* (2006.01)

(52) U.S. Cl.
   CPC ........... *A61B 2018/00589* (2013.01); *A61B 2018/00625* (2013.01); *A61B 2018/207* (2013.01); *A61B 2018/2065* (2013.01); *A61B 2018/20359* (2017.05); *H01S 3/0078* (2013.01); *H01S 3/042* (2013.01); *H01S 3/0407* (2013.01); *H01S 3/11* (2013.01)

(58) Field of Classification Search
   CPC ... A61B 2018/207; A61B 18/20–18/28; H01S 3/005; H01S 3/0078; H01S 3/0407; H01S 3/042; H01S 3/105; H01S 3/109; H01S 3/11

See application file for complete search history.

(56) References Cited

U.S. PATENT DOCUMENTS

| | | | |
|---|---|---|---|
| 6,066,127 A | 5/2000 | Abe | |
| 10,454,237 B2 * | 10/2019 | Yu | .......... H01S 3/105 |
| 2002/0027932 A1 | 3/2002 | Takada | |
| 2006/0126675 A1 * | 6/2006 | Eno | .......... A61B 18/20 372/21 |
| 2013/0190742 A1 * | 7/2013 | Connors | .......... A61B 18/20 606/17 |

FOREIGN PATENT DOCUMENTS

| | | |
|---|---|---|
| CN | 102355875 A | 2/2012 |
| EP | 1184947 A1 | 3/2002 |
| JP | S 62-254117 A | 11/1987 |
| JP | 2000-091678 A | 3/2000 |
| JP | 2002-500526 A | 1/2002 |
| JP | 2007-181634 A | 7/2007 |
| WO | WO 92/04871 A1 | 4/1992 |

* cited by examiner

DUAL WAVELENGTH SURGICAL LASER SYSTEM

CROSS-REFERENCE TO RELATED APPLICATION

This application is a continuation of U.S. patent application Ser. No. 14/964,890, filed Dec. 10, 2015, which claims the benefit of priority from U.S. Provisional Application No. 62/092,380, filed Dec. 16, 2014, the content of each of which is incorporated by reference in its entirety.

BACKGROUND

Laser energy can be put to a variety of beneficial uses, which are wavelength specific. That is, to accomplish one goal or to perform one type of medical procedure, a laser system providing an output at a first wavelength is required. To accomplish another goal or to perform another type of medical procedure, a laser system providing an output at a second wavelength is required.

One such application of laser systems arises in the medical context. For instance, in some surgical procedures, an Nd:YAG laser is used at an output wavelength of 1064 nm to achieve surgical or therapeutic results. Also, such a laser system can be frequency-doubled to provide a 532 nm wavelength output laser energy to accomplish other surgical or therapeutic results.

For example, the 532 nm light is strongly absorbed by hemoglobin in blood making it very effective in cutting and vaporizing vascular tissue. The 1064 nm light is not strongly absorbed in most tissue and penetrates deeply into tissue. With sufficient power at 1064 nm (approximately 20 to 80 Watts) this causes sufficient heating of tissue to coagulate blood, and hence the 1064 nm laser is effective in performing coagulation to reduce or stop bleeding during a surgical procedure. These properties of laser-tissue interaction make a combination 532 nm laser and a 1064 nm laser very useful for surgical applications.

SUMMARY

Embodiments of the present disclosure are directed to a surgical laser system having selectable modes of operation in which laser energies of different wavelengths may be discharged for performing different laser treatments on a patient. In some embodiments, the surgical laser system includes a pump module, a gain medium, a non-linear crystal (NLC), an output, and a first path diversion assembly. The pump module is configured to produce pump energy within an operating wavelength. The gain medium is configured to convert the pump energy into first laser energy. The NLC is configured to convert a portion of the first laser energy into second laser energy, which is a harmonic of the first laser energy. The first path diversion assembly has first and second operating modes. When the first path diversion assembly is in the first operating mode, the first laser energy is directed along the output path to the output, and the second laser energy is diverted from the output path and the output. When the first path diversion assembly is in the second operating mode, the second laser energy is directed along the output path to the output, and the first laser energy is diverted from the output path and the output.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
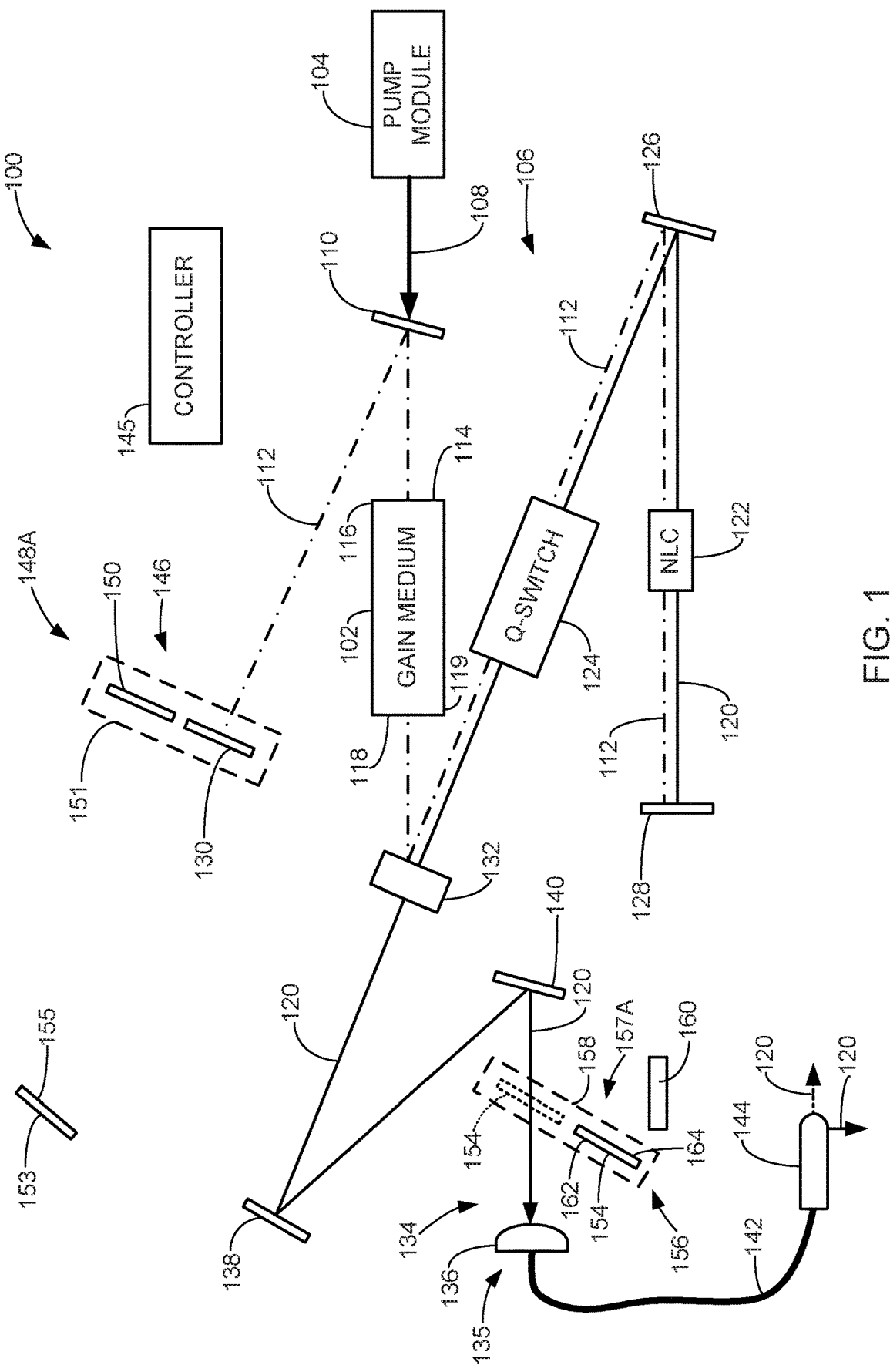
FIGS. 1 and 2 are schematic diagrams of an exemplary surgical laser system respectively operating in a vaporization mode and a coagulation mode, in accordance with embodiments of the invention.

Embodiments of the invention are described more fully hereinafter with reference to the accompanying drawings. Elements that are identified using the same or similar reference characters refer to the same or similar elements. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

Specific details are given in the following description to provide a thorough understanding of the embodiments. However, it is understood by those of ordinary skill in the art that the embodiments may be practiced without these specific details. For example, circuits, systems, networks, processes, frames, supports, connectors, motors, processors, and other components may not be shown, or shown in block diagram form in order to not obscure the embodiments in unnecessary detail.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Embodiments of the present invention may also be described using flowchart illustrations and block diagrams. Although a flowchart may describe the operations as a sequential process, many of the operations can be performed in parallel or concurrently. In addition, the order of the operations may be re-arranged. A process is terminated when its operations are completed, but could have additional steps not included in a figure or described herein.

It is understood that one or more of the blocks (of the flowcharts and block diagrams) may be implemented by computer program instructions. These program instructions may be provided to a processor circuit or controller, such as a microprocessor, microcontroller or other processor, which executes the instructions to implement the functions specified in the block or blocks through a series of operational steps to be performed by the processor(s) and corresponding hardware components.

Embodiments of the present invention are directed to surgical laser systems that are configured to output laser energy at two different wavelengths. In some embodiments, the wavelengths of laser energy output by the system are harmonics of each other. In some embodiments, the systems are configured to output laser energy having a vaporization wavelength (e.g., 532 nm) useful in tissue vaporizing, ablating and cutting operations, and a coagulation wavelength (e.g., 1064 nm) useful in performing a coagulation operation. Thus, a surgeon may use the systems formed in accordance with one or more embodiments described herein to perform a vaporization operation on tissue of a patient by configuring the system to discharge laser energy having the vaporization wavelength, and then perform a coagulation operation on the tissue by configuring the system to discharge laser energy having the coagulation wavelength. In some embodiments, the vaporization wavelength is in the range of approximately 400-600 nm and the coagulation wavelength is in the range of 780 nm-3.0 µm. Embodiments of the surgical laser systems described herein also include configurations for discharging laser energy at other wavelengths.

FIGS. 1-8 are schematic diagrams of exemplary surgical laser systems 100, in accordance with embodiments of the invention. In some embodiments, the system 100 includes a gain medium 102, a pump module 104, and a laser resonator 106. In some embodiments, the gain medium 102 is a doped crystalline host that is configured to absorb pump energy 108 generated by the pump module 104 having a wavelength that is within an operating wavelength (i.e., absorption spectra) range of the gain medium 102. In some embodiments, the gain medium 102 is end-pumped by the pump energy 108, which is transmitted through a folding mirror 110 that is transmissive at the wavelength of the pump energy 108. The gain medium 102 absorbs the pump energy 108 and outputs laser energy 112 at the primary wavelength. In some embodiments, the primary wavelength is within the desired coagulation wavelength range.

The gain medium 102 is water cooled in exemplary embodiments along its sides. In some embodiments, the gain medium 102 includes an undoped end cap 114 bonded on a first end 116 of the gain medium 102, and/or an undoped end cap 118 bonded on a second end 119 of the gain medium 102. In some embodiments, the end 119 is coated so that it is reflective at the pump energy wavelength, while transmissive at a resonant mode of the system 100. In this manner, the pump energy that is unabsorbed at the second end 119 is redirected back through the gain medium 102 to be absorbed.

The pump module 104 produces the pump energy 108 within an operating wavelength range of the gain medium 102. The gain medium 102 converts the pump energy 108 into laser energy 112, which, in some embodiments is within the coagulation wavelength range. The laser resonator 106 is configured to generate laser energy 120 that is a harmonic of the laser energy 112 output from the gain medium 102. In some embodiments, the laser energy 120 is within the vaporization wavelength range. As a result, the system 100 is capable of operating in a vaporization mode, in which the laser energy 120 (vaporization laser energy) is discharged, and a coagulation mode, in which the laser energy 112 (coagulation laser energy) is discharged. In some embodiments, the pump module 104 is operated at a high power level (e.g., greater than 80 W) when the system 100 is in the vaporization mode, and a low power level (e.g., 30 W-80 W) when the system 100 is in the coagulation mode.

It is understood that, while embodiments described herein refer to coagulation laser energy 112 or vaporization laser energy 120, some embodiments include coagulation laser energy 112 that is outside the coagulation wavelength range, and vaporization laser energy 120 that is outside the vaporization wavelength range. These alternative embodiments of the laser energy 112 and 120 may be used to perform laser surgical procedures other than coagulation and vaporization procedures.

In some exemplary embodiments, the gain medium 102 comprises a yttrium-aluminum-garnet crystal (YAG) rod with neodymium atoms dispersed in the YAG rod to form a Nd:YAG gain medium 102. The Nd:YAG gain medium 102 converts the pump energy 108 into the coagulation laser energy 112 having a primary wavelength of 1064 nm.

In some exemplary embodiments, the laser resonator 106 includes a non-linear crystal (NLC) 122, such as a lithium tri borate (LBO) crystal or a potassium titanyl phosphate crystal (KTP), for generating the vaporization laser energy 120, which is a second harmonic of the laser energy 112 emitted by the gain medium 102 having a wavelength of 532 nm.

In some embodiments, the laser resonator 106 includes a Q-switch 124 that operates to change the laser energy 112 into a train of short pulses with high peak power to increase the conversion efficiency of the second harmonic laser beam. In some embodiments, the laser resonator 106 includes reflecting mirrors 126, 128 and 130 (e.g., mirror 130 may be used in select modes), the folding mirror 110, and an output coupler 132. The mirrors 110, 126, 128 and 130, and output coupler 132 are highly reflective at the primary wavelength (e.g., 1064 nm). The output coupler 132 is highly transmissive at the second harmonic output wavelength (e.g., 532 nm). Therefore, in vaporization mode, the primary wavelength laser energy 112 (e.g., 1064 nm) inside the resonator 106 bounces back and forth along the path between the mirrors 128 and 130, passing through the gain medium 102 and the non-linear crystal 122 to be frequency doubled to the second harmonic output wavelength (e.g., 532 nm) laser energy 120, which is discharged through output coupler 132.

This configuration using the Nd:YAG gain medium 102 and a LBO non-linear crystal 122 produces a frequency converted output laser energy 120 having a wavelength of 532 nm, as indicated above.

Figure 2:
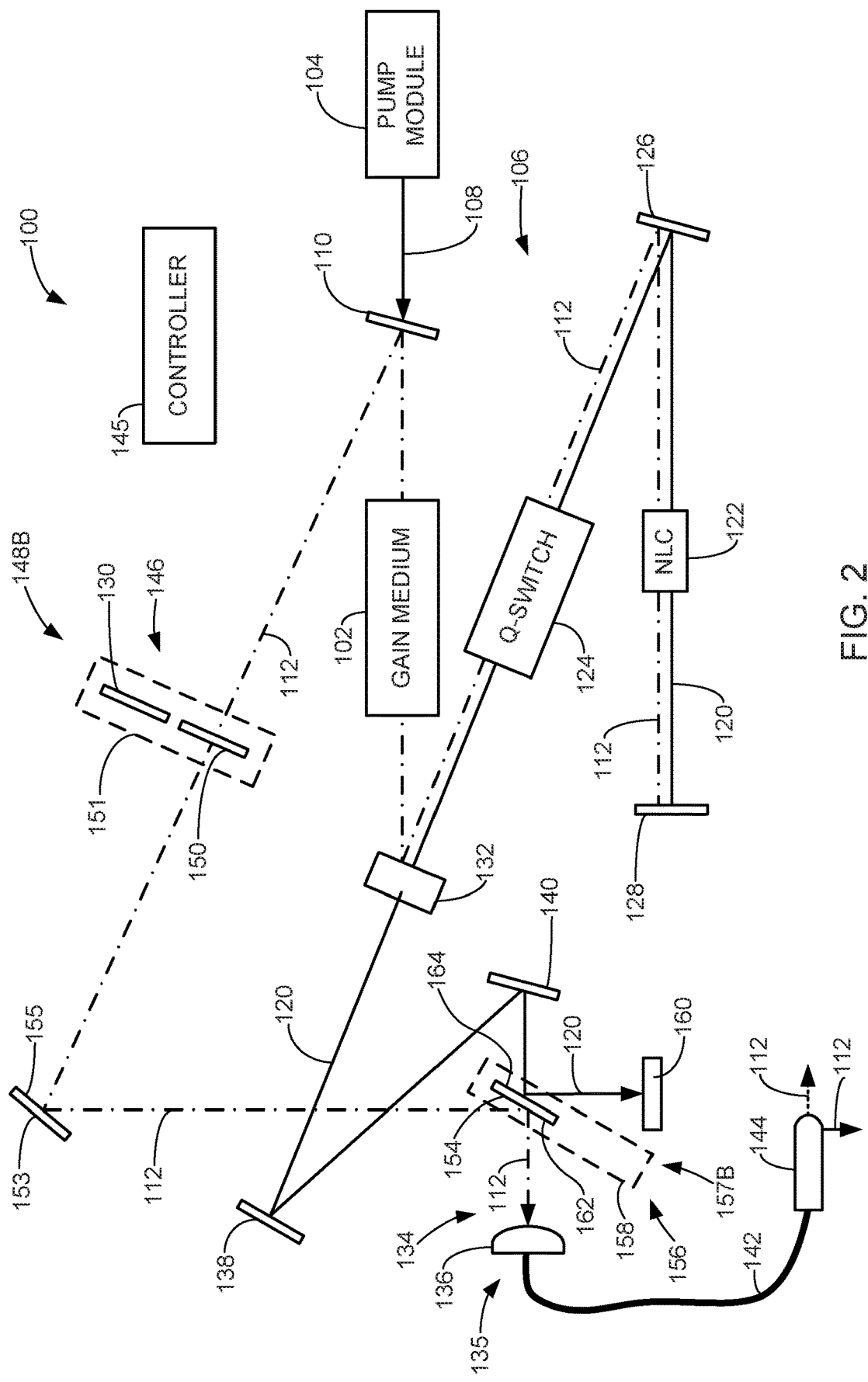

The system 100 selectively discharges the laser energies 112 and 120 along an output path 134 to an output 135. In some embodiments, the output 135 includes an optical coupler 136 that optically couples the laser energy 112 or 120 to a waveguide, such as an optical or laser fiber 142, as shown in FIGS. 1 and 2. In some embodiments, the system 100 includes a laser delivery device 144 that is configured to discharge the laser energy 112 or 120 to the targeted tissue. In some embodiments, the device 144 is configured to discharge the laser energy 112 or 120 either laterally, i.e., side firing, (solid arrow) or along a longitudinal axis of the device 144, i.e., end-firing (dashed arrow), in accordance with conventional techniques. In some embodiments, the device 144 may be supported within an endoscope or other conventional surgical tool.

In some embodiments, the surgical laser system 100 includes a controller 145, which represents one or more processors. The controller 145 is configured to execute program instructions and/or process inputs (e.g., control module, foot pedal, etc.) from a user of the system to control components of the system to perform one or more functions described herein, such as switching the system between the vaporization and coagulation modes including, for example, activating or controlling motion stages to move mirrors of the system, and adjust the paths of the vaporization and coagulation laser energies through the system.

FIGS. 1 and 2 respectively illustrate system 100 in the vaporization mode and the coagulation mode, in accordance with embodiments of the invention. In some embodiments, system 100 includes a path diversion assembly 146 having an operating mode or position 148A, in which the vaporization laser energy 120 is directed along the output path 134 to the output 135, and the coagulation laser energy 112 is diverted from the output 135, as shown in FIG. 1. Thus, in some embodiments, the operating mode 148A of the path diversion assembly 146 facilitates the vaporization laser mode of system 100.

In some embodiments, the path diversion assembly 146 includes an operating mode or position 148B, in which the coagulation laser energy 112 is directed along the output path 134 to the output 135, and the vaporization laser energy 120 is diverted from the output, as shown in FIG. 2. Thus, in some embodiments, the operating mode 148B of the path diversion assembly 146 facilitates the coagulation laser mode of system 100.

In some embodiments, the path diversion assembly 146 includes the mirror 130, a mirror 150, and a precise motion stage 151. When the assembly 146 is in the mode 148A (FIG. 1), the mirror 130 is moved into the path of the laser energy 112 using the precise motion stage 151. In some embodiments, the mirror 130 includes a surface coating that is highly reflective of the coagulation laser energy 112. As discussed above, because mirror 130 is highly reflective with respect to the coagulation laser energy 112, the laser energy 112 inside the resonator 106 bounces back and forth along the path between the mirrors 128 and 130, passing through the gain medium 102 and the non-linear crystal 122, which causes the laser energy 112 to be frequency doubled to the second harmonic output wavelength or vaporization laser energy 120. In some embodiments, the vaporization laser energy 120 is transmitted through the output coupler 132, and directed to the output path 134 and the output 135 for delivery to targeted tissue of a patent through the delivery device 144, when assembly 146 is in the mode 148A, as shown in FIG. 1. The coagulation laser energy 112 is diverted from the output path 134 and is substantially contained within the resonator 106 when the assembly 146 is in the mode 148A, as shown in FIG. 1.

The path diversion assembly 146 may be placed in the mode 148B to place the system 100 in the coagulation mode shown in FIG. 2, in which the coagulation laser energy 112 is directed along the output path 134, and through the output 135. In some embodiments, the path diversion assembly 146 is transitioned from the mode 148A to the mode 148B by switching the mirror 130 with the mirror 150 using the motion stage 151. In some embodiments, the mirror 150 includes a coating that is highly transmissive to the coagulation laser energy 112, and is highly reflective of the vaporization laser energy 120. Thus, the vaporization laser energy 120 is reflected by the mirror 150 back to the mirror 110, and is discharged from the resonator 106 through the output coupler 132. In some embodiments, the laser energy 120 is diverted away from the output path 134 and the output 135, such as to an energy dump 160, as discussed below.

In some embodiments, the coagulation laser energy 112 that is transmitted through the mirror 150 is directed to the output path 134 and the output 135 through routing mirrors 153 and 154, when the path diversion assembly 146 is in the mode 148B, as shown in FIG. 2. In some embodiments, the position of the mirror 153 is fixed, and the curvature of the surface 155 of the mirror 153 is preferably optimized to maximize the fiber coupling efficiency. In one exemplary embodiment, the coating parameters for the surface 155 are selected to be highly reflective (e.g., 99.9%) of the coagulation laser energy for example. The coagulation laser energy 112 may then be delivered to targeted tissue or object of a patient through the delivery device 144.

In some embodiments, system 100 includes a path diversion assembly 156 having an operating mode or position 157A, in which the vaporization laser energy 120 directed to the output 135 through the output path 134, while the coagulation laser energy is diverted from the output path 134, as shown in FIG. 1. Thus, in some embodiments, the operating mode 157A of the path diversion assembly 156 facilitates the vaporization laser mode of system 100. In some embodiments, the assembly 156 has an operating mode or position 157B, in which the coagulation laser energy is directed to the output 135 through the output path 134, while the vaporization laser energy 120 is diverted from the output path, as shown in FIG. 2. Thus, in some embodiments, the operating mode 157B of the path diversion assembly 156 facilitates the coagulation laser mode of system 100.

In some embodiments, the path diversion assembly 156 includes the output mirror 154 and a precise motion stage 158. When in the operating mode 157A, the mirror 154 is moved out of the path of the vaporization laser energy 120 using the motion stage 158, as illustrated in FIG. 1. This allows the vaporization laser energy 120 to travel along the output path 134 to the output 135 without interference from the mirror 154.

In some embodiments, when the path diversion assembly 156 is in the mode 157B, the output mirror 154 is moved into the paths of the coagulation laser energy 112 and the vaporization laser energy 120, as shown in FIG. 2. In some embodiments, the coagulation laser energy 112 is directed along the output path by the mirror 154 to the output 135, and the vaporization laser energy 120 is diverted from the output path 134 by the mirror 154. In some embodiments, the vaporization laser energy 120 is diverted by the mirror 154 to an energy dump 160 that absorbs the vaporization laser energy 120 to contain it within the laser system 100. This can be achieved, for example, by (a) including a coating on the surface 162 of the mirror 154 that is highly reflective of the coagulation laser energy 112 and (b) including a coating on the surface 164 of the mirror 154 that is highly reflective of the vaporization energy 120.

Thus, in some embodiments of the vaporization mode (FIG. 1), the path diversion assembly 146 positions the mirror 130 into the path of the coagulation energy 112 using the motion stage 151, and the path diversion assembly 156 moves the mirror 154 out of the path of the vaporization energy 120 using the motion stage 158. As a result, the vaporization laser energy 120 is directed along the output path 134 to the output 135. The laser energy 120 at the output 135 may be coupled to the delivery device 144, and discharged as desired to perform a surgical laser treatment on a patient. Additionally, the coagulation laser energy 112 is reflected back through the gain medium 102, and the resonant cavity 106, which, as described above, causes the primary laser energy 112 to be frequency doubled to the second harmonic output wavelength thereby generating the vaporization laser energy 120, which is discharged from the laser system along the output path 134, and through the output 135. Thus, the coagulation laser energy 112 is diverted from the output path 134 and the output 135.

In some embodiments of the coagulation mode (FIG. 2), the path diversion assembly 146 moves the mirror 150 into the path of the coagulation laser energy 112 using the motion stage 151, and the path diversion assembly 156 moves the mirror 154 into the path of both the coagulation laser energy 112 and the vaporization laser energy 120 using the motion stage 158. As a result, the coagulation laser energy 112 is directed along the output path 134 to the output 135. The laser energy 112 may be coupled to the delivery device 144 and discharged as desired to perform a surgical laser treatment on a patient. Additionally, the vaporization laser energy 120 is diverted from the output path 134 and the output 135, such as to the energy dump 160, for example.

The precise motion stage 151 of the path diversion assembly 146, and the precise motion stage 158 of the path diversion assembly 156, are used to selectively position the mirrors 130 and 150 in the modes 148A and 148B, and the mirror 154 in the modes 157A and 157B. In some embodiments, the precise motion stages 151, 158 are motorized and may take on any suitable form. In some embodiments, the precise motion stages 151 and/or 158 are in the form of a rotation stage, in which the corresponding mirrors 130, 150 and 154 are rotated about an axis to place them in their operative modes. In some embodiments, the precise motion stages 151 and/or 158 are step stages, in which the mirrors 130, 150 and 154 are moved laterally, or pivoted to place them in their operative modes. Other suitable motion stages 151, 158 may also be used, as is readily understood by those of ordinary skill in the art.

In some embodiments, the system 100 does not utilize the path diversion assembly 156. Instead, the mirror 154 has a fixed position that is in line with the discharge path of the vaporization laser energy 120, as represented in phantom lines in FIG. 1. In this embodiment, the mirror 154 is highly transmissive to the vaporization laser energy 120, and includes a surface 162 that is highly reflective of the coagulation laser energy 112.

Figure 3:
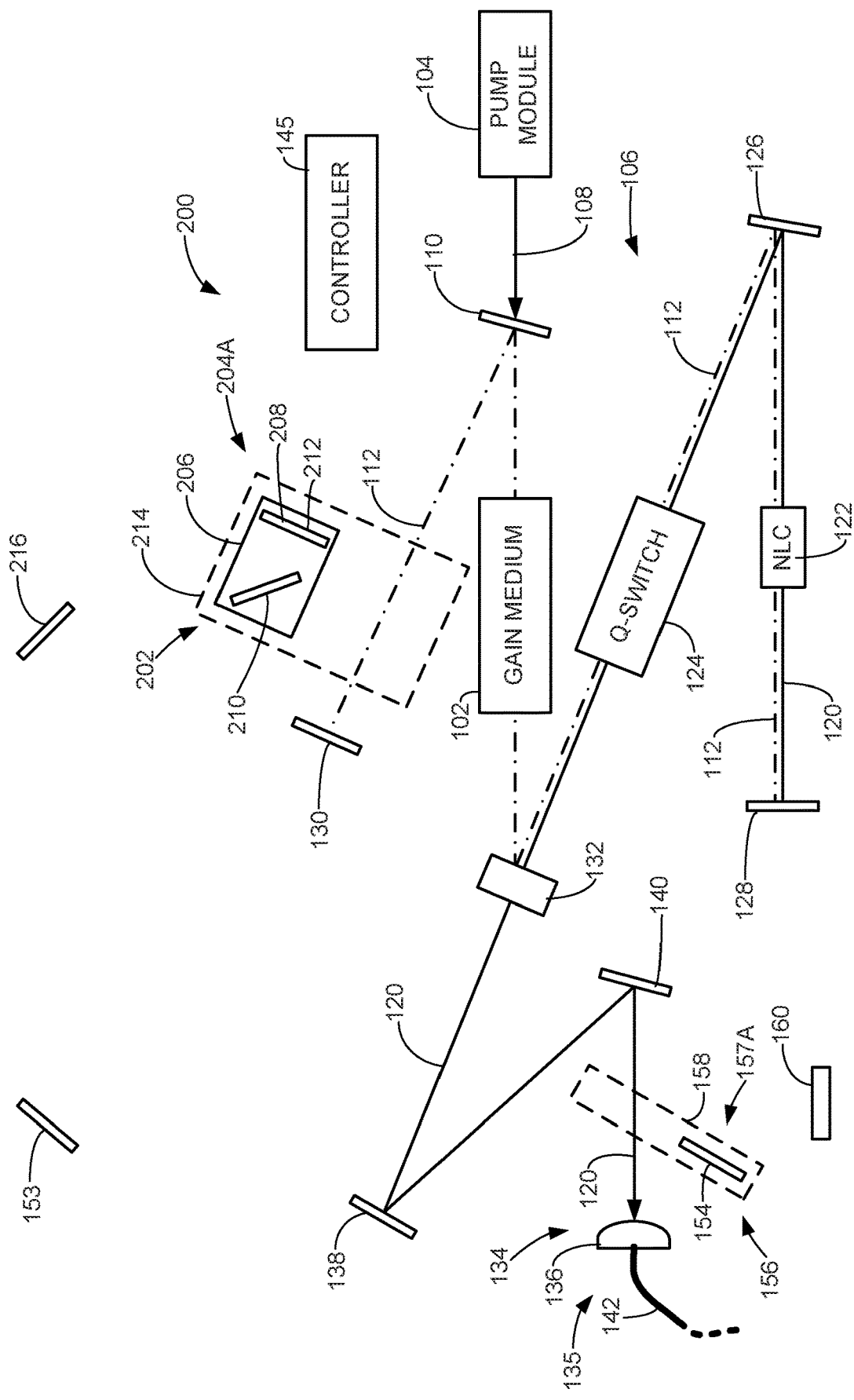
FIGS. 3 and 4 are schematic diagrams of an exemplary surgical laser system respectively in vaporization and coagulation modes, in accordance with embodiments of the invention.
Figure 4:
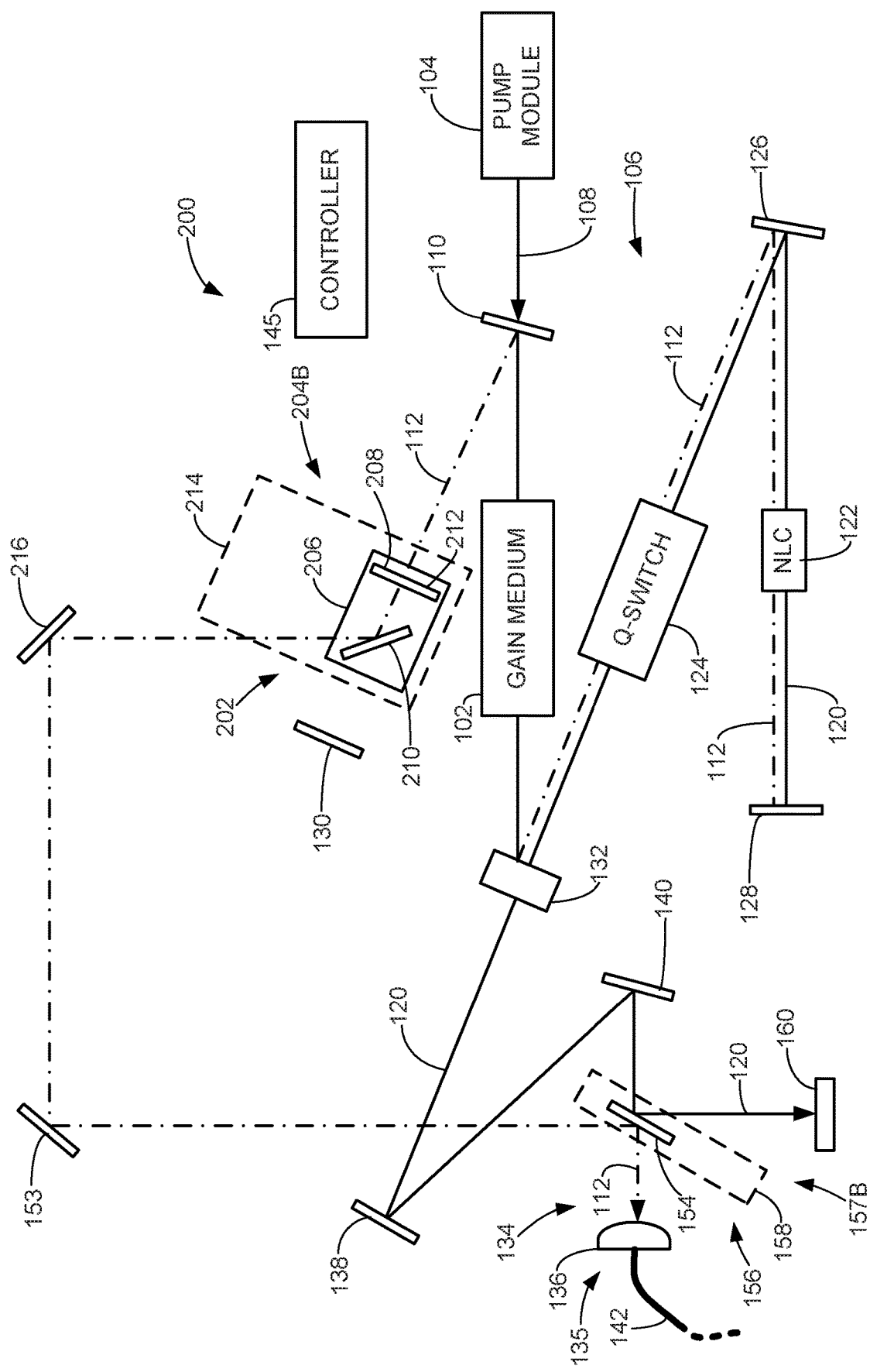

FIGS. 3 and 4 are schematic diagrams of an exemplary surgical laser system 200 respectively in vaporization and coagulation modes, in accordance with embodiments of the invention. The system 200 operates similarly to the system 100 of FIGS. 1 and 2, except for the manner in which the system 200 is switched from the vaporization mode (FIG. 3) to the coagulation mode (FIG. 4). Elements that operate in a similar manner, or that perform a similar function to those described with respect to FIGS. 1 and 2, use the same element numbers as used in describing FIGS. 1 and 2. In some embodiments, the mirror 130 and each of the other components that are responsible for outputting the vaporization laser energy 120 when the system 200 is in the vaporization mode have a fixed position. As a result, alignment between the components that control the path of the vaporization laser energy can be accurately maintained.

In some embodiments, the system 200 includes a path diversion assembly 202 having an operating mode or position 204A (FIG. 3) corresponding to a vaporization mode of the system 200, and an operating mode or position 204B (FIG. 4) corresponding to a coagulation mode of the system 200. When the path diversion assembly 202 is in the mode 204A, the vaporization laser energy 120 is directed to the output path 134 and to the output 135 for use in performing a surgical laser treatment using the delivery device 144 (FIGS. 1 and 2) that is attached to the laser fiber 142, for example. The coagulation laser energy 112 is diverted from the output path 134 by retaining the laser energy 112 within the laser resonator 106 by the mirrors 128 and 130, for example, as shown in FIG. 3.

In some embodiments, the system 200 includes an assembly 206 containing mirrors 208 and 210 that are positioned outside the path of the laser energy 112 when the path diversion assembly 202 is in the mode 204A, as shown in FIG. 3. In some embodiments, the mirror 208 includes a coating on a surface 212 that is highly transmissive to the coagulation laser energy 112, and is highly reflective to the vaporization laser energy 120. In some embodiments, the path diversion assembly 202 includes a precise motion stage 214 that is configured to move the assembly 206 between the modes or positions 204A and 204B. Embodiments of the motion stage 214 include those discussed above with regard to the motion stages 151 and 158.

When the path diversion assembly 202 is in the operating mode 204B (FIG. 4) corresponding to the coagulation mode, the assembly 206 is moved into the path of the laser energy 112 using the motion stage 214. At least a portion of the coagulation laser energy 112 is transmitted through the mirror 208 and is directed to the output path 134 and to the output 135, using the mirror 210. One or more routing mirrors may be used to deliver the coagulation laser energy 112 to the output path 134. For example, a routing mirror 216 may be used to direct the coagulation laser energy 112 reflected from mirror 210 to the mirror 153 and the mirror 154 to deliver the coagulation laser energy 112 to the output path 134. As with system 100, the mirror 154 may have a fixed position, or be moved using a suitable precise motion stage 158, as discussed above. The coagulation laser energy 112 may then be used in performing a surgical laser treatment using the delivery device 144 (FIGS. 1 and 2), for example. The vaporization laser energy 120 is reflected by the mirror 210 to divert the laser energy 120 from the output path 134, and retain the laser energy 120 within the laser resonator 106, as shown in FIG. 4.

Figure 5:
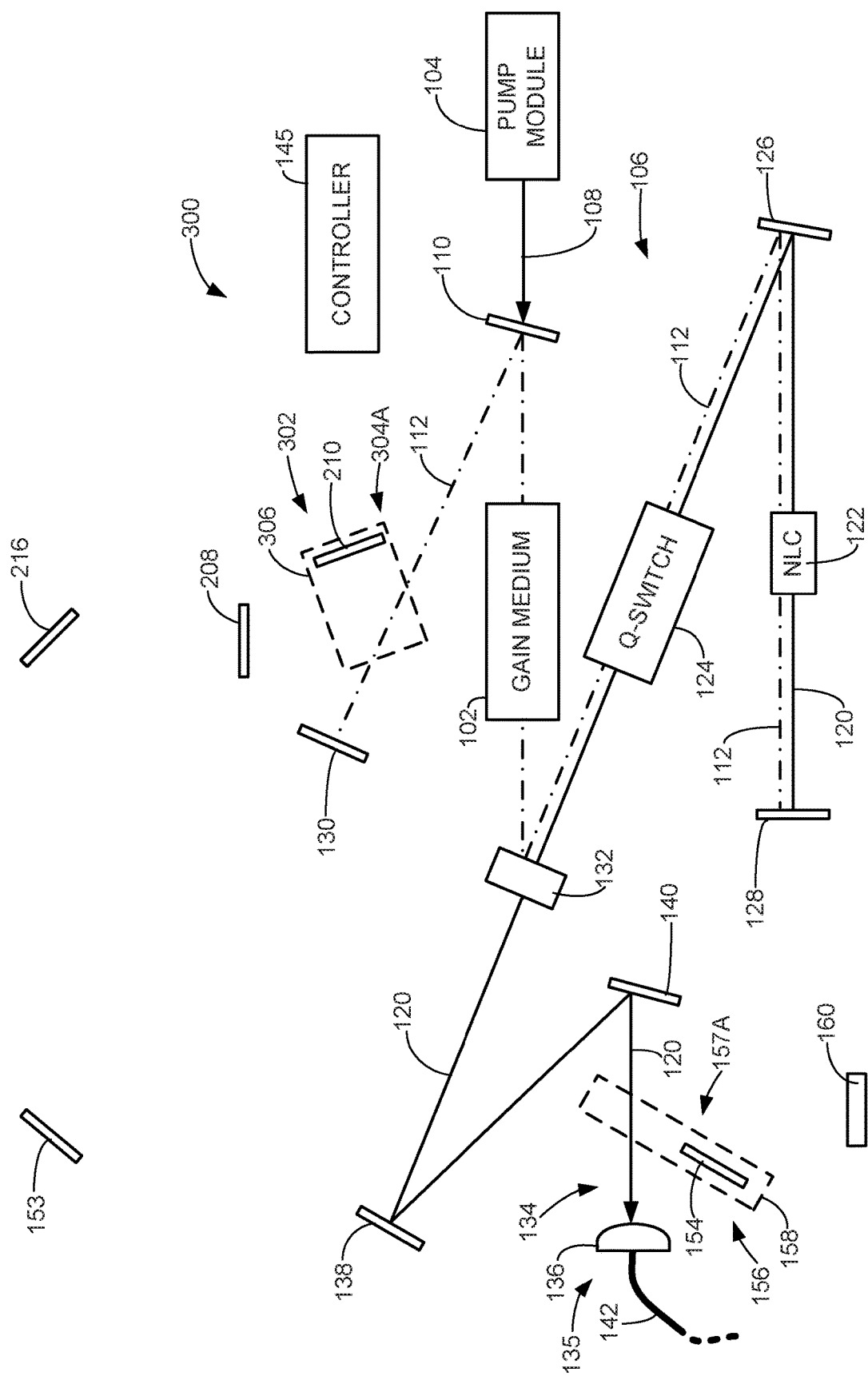
FIGS. 5 and 6 are schematic diagrams of an exemplary surgical system respectively in vaporization and coagulation modes, in accordance with embodiments of the invention.
Figure 6:
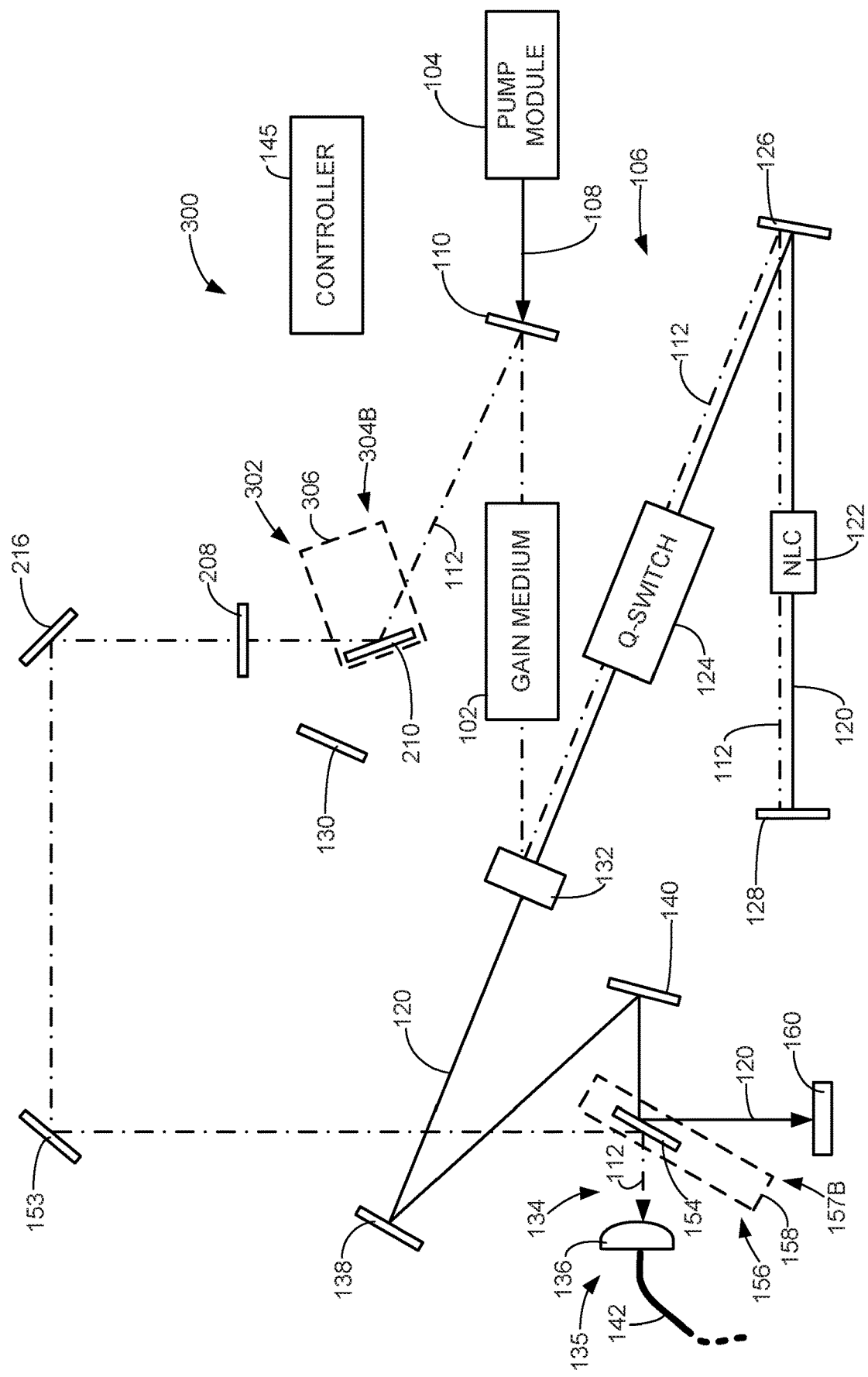

FIGS. 5 and 6 are schematic diagrams of an exemplary surgical system 300 respectively in vaporization and coagulation modes, in accordance with embodiments of the invention. The system 300 operates similarly to the systems 100 and 200 described above, except for the manner in which the system 300 is switched from the vaporization mode (FIG. 5) to the coagulation mode (FIG. 6). Elements that are the same or similar elements, or perform the same or similar function to those described above with reference to FIGS. 1-4, are labeled using the same or similar reference numbers.

In some embodiments, the system 300 includes a path diversion assembly 302 having an operating mode or position 304A (FIG. 5) corresponding to the vaporization mode, and an operating mode or position 304B (FIG. 6) corresponding to the coagulation mode. In some embodiments, the path diversion assembly 302 includes the routing mirror 210, and is configured to move the mirror 210 between two positions corresponding to the modes 304A and 304B to transition the system 300 between the vaporization and coagulation modes, respectively, while the mirror 208 remains in a fixed position. In some embodiments, the path diversion assembly 302 moves the mirror 210 between the positions of modes 304A and 304B using a precise motion stage 306, which may be formed in accordance with the precise motion stages 151 and 158 described above.

When the path diversion assembly 302 is in the mode 304A, the mirror 210 is positioned out of the path of the coagulation laser energy 112. As a result, the coagulation laser energy 112 is diverted from traveling to the output path 134, and is retained within the laser resonator 106 by mirrors 128 and 130, for example, as shown in FIG. 5. The coagulation laser energy 112 is converted to the vaporization laser energy 120 within the laser resonator 106, and is directed to the output path 134 and to the output 135, in accordance with embodiments described herein, as shown in FIG. 5. The vaporization laser energy 120 may be coupled to the delivery device 144 (FIGS. 1 and 2) and discharged as desired to perform a laser treatment on a patient, for example.

When the path diversion assembly 302 is in the mode 304B, the mirror 210 is moved into the path of the coagulation laser energy 112 using the motion stage 306, as shown in FIG. 6. The laser energy 112 is reflected off the mirror 210 toward the fixed mirror 208. Since the mirror 208 is at least partially transmissive of the wavelengths of the laser energy 112, at least a portion of the laser energy 112 that passes through the mirror 208 is routed to the output path 134 and the output 135. For example, the coagulation laser energy 112 may be routed to the output path by the mirrors 216, 153 and 154 to the output path 134 and the output 135, in accordance with embodiments described herein. As with system 100, the mirror 154 may have a fixed position, or be moved using a suitable precise motion stage 158, as discussed above. The coagulation laser energy 112 may then be used in performing a surgical laser treatment using the delivery device 144 (FIGS. 1 and 2), for example. The portion of the coagulation laser energy 112 that does not pass through the mirror 208 is reflected back toward the mirror 210, and is retained within the laser resonator 106.

Figure 7:
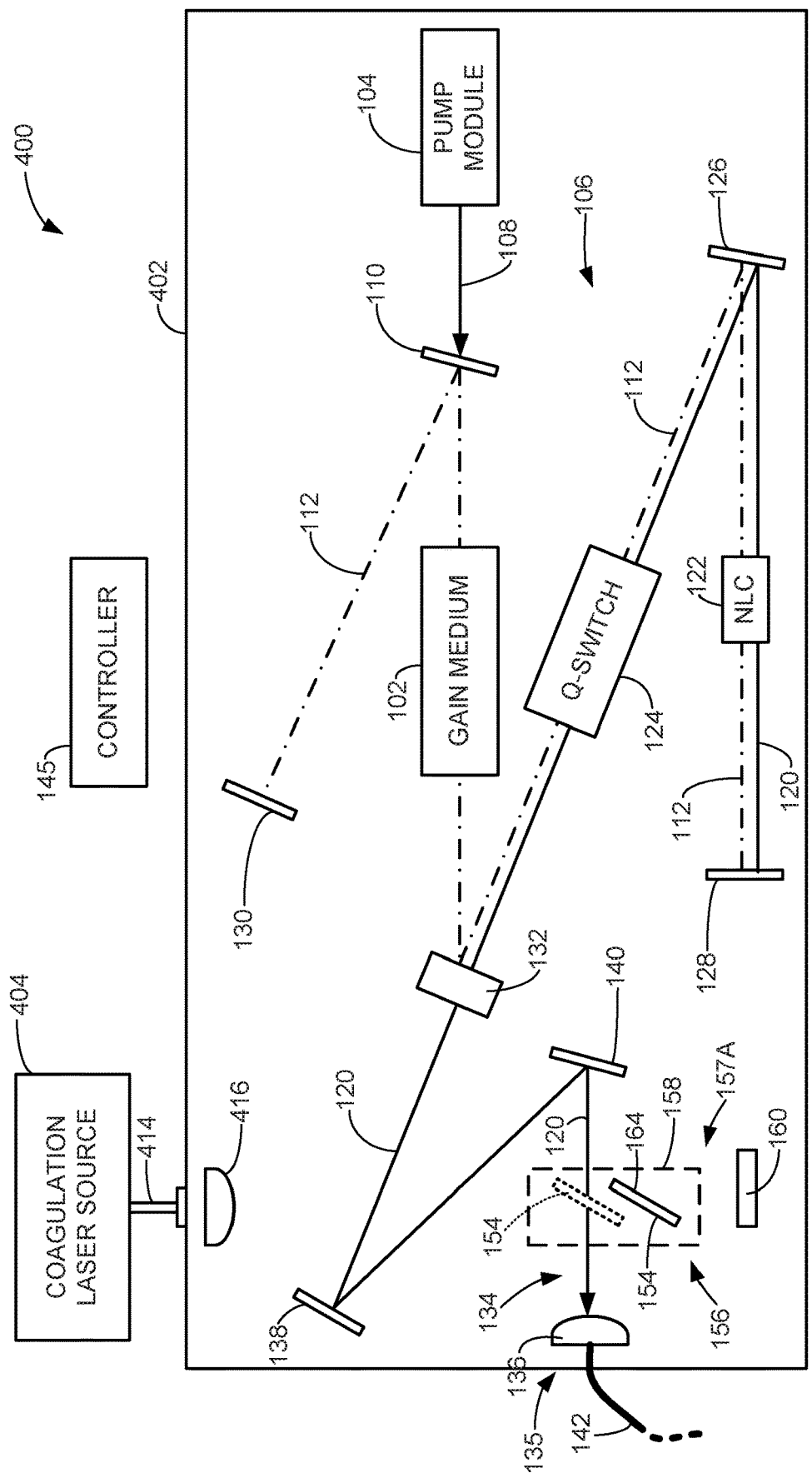
FIGS. 7 and 8 are schematic diagrams of an exemplary surgical laser system respectively in vaporization and coagulation modes, in accordance with embodiments of the invention.
Figure 8:
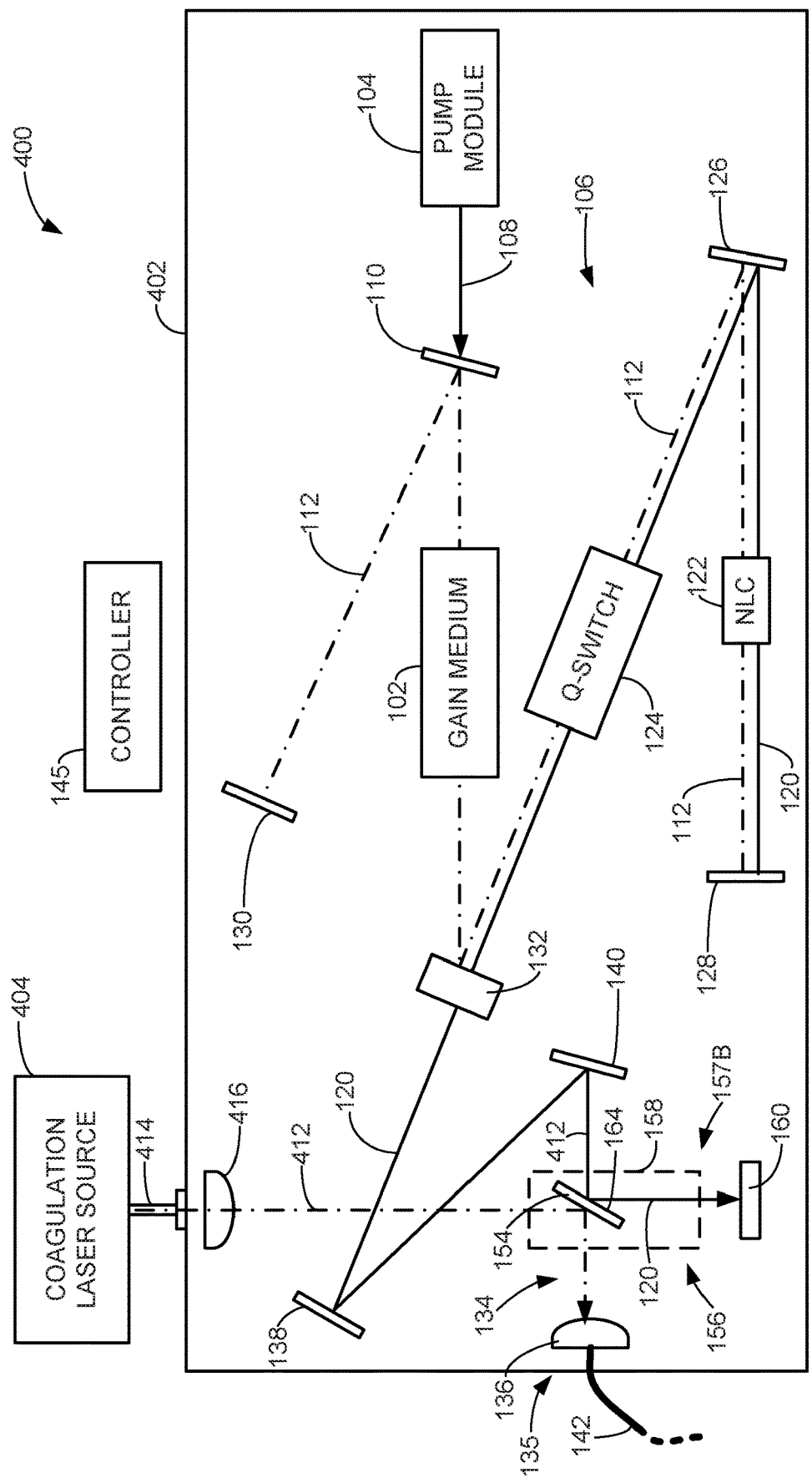

FIGS. 7 and 8 are schematic diagrams of an exemplary surgical laser system 400 respectively in vaporization and coagulation modes, in accordance with embodiments of the invention. In this embodiment, the system 400 includes a laser cavity 402 that is configured to discharge the vaporization laser energy 120 when in a vaporization mode, as shown in FIG. 7. In some embodiments, the components of the laser cavity 402 are fixed resulting in an operation similar to the vaporization mode of the system 200.

In some embodiments, the system 400 includes a coagulation laser source 404 that is configured to discharge the desired coagulation laser energy 412 when the system 400 is in a coagulation mode, as shown in FIG. 8. In some embodiments, the coagulation laser source 404 includes one or more laser diodes that are coupled to the laser cavity 402 through a suitable optical fiber 414. The coagulation laser energy 412 may have a low power relative to the vaporization laser energy 120, such as a power ranging between 20 W-50 W, for example. A collimation lens 416 may be used to collimate the coagulation laser energy 412.

In some embodiments, the system 400 is transitioned from the vaporization mode to the coagulation mode by activating the coagulation laser source 404. The coagulation laser energy 412 is reflected off the mirror 154 to direct the coagulation laser energy 412 to the output path 134 and the output 135 for discharge from the system 400 through the delivery device 144 (FIGS. 1 and 2) to perform a laser treatment on a patient, for example.

In some embodiments, the mirror 154 has a fixed position, as indicated by the phantom line box of FIG. 7, and is highly transmissive to the vaporization laser energy 120 and highly reflective of the coagulation laser energy 412, such as described above with reference to FIG. 1. In some embodiments, the system 400 is transitioned from the vaporization mode to the coagulation mode by deactivating the pump module 104, or blocking the delivery of the pump energy 108 to the gain medium 102, and activating the coagulation laser source 404.

In some embodiments, the mirror 154 is movable between the operating mode or position 157A (FIG. 7) corresponding to the vaporization mode, and the operating mode or position 157B (FIG. 8) corresponding to the coagulation mode using, for example, the motion stage 158 of the path diversion assembly 156. When the system 400 is in the vaporization mode, the mirror 154 is moved to the position or mode 157A, as indicated by the solid box in FIG. 7. The system 400 is transitioned to the coagulation mode by moving the mirror 154 into the position corresponding to the mode 157B using the precise motion stage 158, and activating the laser source 404, as shown in FIG. 8.

In some embodiments, the mirror 154 has a surface 164 that is highly reflective of the vaporization laser energy 120. In some embodiments, the pump module 104 is maintained in an activated state when the system 400 is in the coagulation mode, and the vaporization laser energy 120 is reflected off the mirror 154 to a beam dump 160, as shown in FIG. 8.

Some embodiments of the present invention are directed to methods of performing a medical laser treatment using the systems 100, 200, 300 and 400. In some embodiments, a physician places the system in the vaporization mode to discharge vaporization laser energy 120 and perform a cutting, vaporization, ablation, or other laser treatment on targeted tissue of a patient using the vaporization laser energy 120. After performing the laser treatment, it may be desirable to perform a coagulation operation on the targeted tissue. In some embodiments, the physician switches the system from the vaporization mode to the coagulation mode to discharge coagulation laser energy (112, 412), and deliver the coagulation laser energy to targeted tissue to perform the coagulation operation.

In some embodiments, the switching of the systems described herein between the vaporization mode and the coagulation mode may be performed through an input device, such as a foot pedal, or other suitable input device. In some embodiments, the controller 145 receives the input from the input device and responsively sets the system in the desired mode. In some embodiments, the controller 145 controls one or more motors to drive the various motion stages (e.g., 151, 158, 214, and 306) to move components between various modes, activates or deactivates components (e.g., pump module 104, laser source 404), and/or performs other automated functions. In some embodiments, the transition of the systems between their vaporization and coagulation modes requires an operator to physically move one or more of the motion stages.

Although the present invention has been described with reference to preferred embodiments, workers skilled in the art will recognize that changes may be made in form and detail without departing from the spirit and scope of the invention.

What is claimed is:

1. A surgical laser system comprising:
a pump module configured to produce a pump energy for generating a first laser energy;
a laser source configured to produce a second laser energy;
an output; and
a path diversion assembly having a first operating mode, in which the first laser energy is directed from the pump module to the output, and a second operating mode, in which the second laser energy is directed from the laser source to the output;
wherein the pump module is configured to produce the pump energy in the first operation mode and the second operation mode, and the laser source is configured to produce the second laser energy only in the second operation mode.

2. The surgical laser system of claim 1, wherein the path diversion assembly includes an output mirror which is reflective to both the first laser energy and the second laser energy.

3. The surgical laser system of claim 2, further comprising a processor, wherein the path diversion assembly further includes a motion stage attached to the output mirror, and the processor is configured to control the motion stage so the output mirror is in a first position in the first operating mode and the output mirror is in a second position in the second operating mode.

4. The surgical laser system of claim 3, wherein the processor is configured to control the motion stage so the output mirror is positioned between an output path of the first laser energy and the output in the second position.

5. The surgical laser system of claim 2, wherein the path diversion assembly includes a beam dump, and the output mirror reflects the first laser energy to the beam dump and reflects the second laser energy to the output in the second operation mode.

6. The surgical laser system of claim 1, further comprising a processor configured to control the pump module to produce only the pump energy in the first operating mode, and to control the laser source to produce only the second laser energy in the second operating mode.

7. The surgical laser system of claim 1, wherein the first laser energy is configured to perform a vaporization operation, and the second laser energy is configured to perform a coagulation operation.

8. The surgical laser system of claim 1, further comprising:
a waveguide optically coupled to the output; and
a delivery device at a distal end of the waveguide and configured to discharge the first laser energy or the second laser energy to a target site.

9. The surgical laser system of claim 1, wherein the first laser energy has a wavelength of 400 nm to 600 nm, and the second laser energy has a wavelength of 780 nm to 3.0 μm.

10. The surgical laser system of claim 1, further comprising a gain medium configured to convert the pump energy to the first laser energy.

11. A surgical laser system comprising:
a first laser source configured to generate a first laser energy having a wavelength of 400 nm to 600 nm;
a second laser source configured to produce a second laser energy having a wavelength of 780 nm to 3.0 μm;
an output;
a path diversion assembly comprising:
an output mirror,
a first operating mode, in which the output mirror is in a first position, and
a second operating mode, in which the output mirror is in a second position; and
a controller coupled to the first laser source, the second laser source, and the path diversion assembly, wherein the controller is configured to control the first laser source to generate the first laser energy in both the first operating mode and the second operating mode, and to control the second laser source to generate the second laser energy only in the second operating mode, and wherein the controller is configured to direct the output mirror between the first and second positions.

12. The surgical laser system of claim 11, wherein the first laser energy is configured to perform a vaporization operation, and the second laser energy is configured to perform a coagulation operation.

13. The surgical laser system of claim 11, wherein the path diversion assembly further includes a beam dump, and the output mirror reflects the first laser energy to the beam dump and reflects the second laser energy to the output in the second operation mode.

* * * * *